United States Patent [19]

Ellwood et al.

[11] Patent Number: 5,563,051
[45] Date of Patent: *Oct. 8, 1996

[54] PRODUCTION OF HYALURONIC ACID

[75] Inventors: Derek C. Ellwood, Cumbria; Charles Gervase T. Evans, Salisbury; Geoffrey M. Dunn, Livingston; Neil McInnes, Peebles; Richard G. Yeo; Keith J. Smith, both of Edinburgh, all of United Kingdom

[73] Assignee: Fermentech Medical Limited, Edinburgh, Scotland

[*] Notice: The term of this patent shall not extend beyond the expiration date of Pat. No. 5,411,874.

[21] Appl. No.: 377,265

[22] Filed: Jan. 24, 1995

Related U.S. Application Data

[63] Continuation of Ser. No. 50,046, Jul. 6, 1993, Pat. No. 5,411,874.

[30] Foreign Application Priority Data

Nov. 7, 1990 [GB] United Kingdom ................. 9024223

[51] Int. Cl.$^6$ .................. C12P 19/04; C12P 19/26; C12N 1/20
[52] U.S. Cl. .................. 435/101; 435/84; 435/252.1; 435/885; 536/55.1
[58] Field of Search .................. 435/84, 252.1, 435/885, 101; 536/55.1

[56] References Cited

U.S. PATENT DOCUMENTS

| | | | |
|---|---|---|---|
| 4,517,295 | 5/1985 | Bracke et al. | 435/101 |
| 4,780,414 | 10/1988 | Nimrod et al. | 435/101 |
| 4,801,539 | 1/1989 | Akasaka et al. | 435/101 |
| 4,851,521 | 7/1989 | Valle et al. | 536/55.1 |
| 4,897,349 | 1/1990 | Swann et al. | 435/101 |
| 5,023,175 | 6/1991 | Hosoya et al. | 435/101 |
| 5,071,751 | 12/1991 | Morita et al. | 435/101 |
| 5,093,487 | 3/1992 | Brown et al. | 536/55.1 |
| 5,202,431 | 4/1993 | Valle et al. | 536/55.1 |
| 5,411,874 | 5/1995 | Ellwood et al. | 435/84 |

FOREIGN PATENT DOCUMENTS

| | | |
|---|---|---|
| 144019 | 6/1985 | European Pat. Off. . |
| 244757 | 11/1987 | European Pat. Off. . |
| 363561 | 4/1990 | European Pat. Off. . |
| 62-32893 | 2/1987 | Japan . |
| 843302 | 8/1984 | WIPO . |
| 864355 | 7/1986 | WIPO . |

OTHER PUBLICATIONS

*English Language Abstract of JP 62-032893 (English Language Abstract only submitted).

*Primary Examiner*—Herbert J. Lilling
*Attorney, Agent, or Firm*—Hale and Dorr

[57] ABSTRACT

A process for the production of hyaluronic acid by continuous fermentation of Streptococcus in a chemostat culture gives high yields of high molecular weight hyaluronic acid uncontaminated by toxic impurities. The process is advantageous in that it solves the problem of traditional batch cultures in which degradation enzymes can begin to break down the cell walls of Streptococcus releasing cells contents into the fermenter broth complicating the purification of high molecular hyaluronic acid.

27 Claims, No Drawings

PRODUCTION OF HYALURONIC ACID

This application is a continuation of application Ser. No. 08/050,046, filed 06 Jul. 1993, now U.S. Pat. No. 5,411,874.

The present invention relates to a process for the production of hyaluronic acid (HA) by bacterial fermentation.

HA is a member of a class of polymers known as glycosaminoglycans. HA is a long chain linear polysaccharide and is usually present as the sodium salt which has a molecular formula of $(C_{14}H_2ONNaO_{11})_n$ where n can vary according to the source, isolation procedure and method of determination. However, molecular weights of up to $14 \times 10^6$ have been reported.

HA and its salts can be isolated from many sources including nearly all connective matrices of vertebrate organisms. However, HA is also a capsular component of bacteria such as Streptococci as was shown by Kendall et al, (1937), *Biochem. Biophys. Acta*, 279, 401–405.

HA is non-immunogenic and therefore has great potential in medicine. HA having a high molecular weight (over 1 million) has been found to be particularly useful because of its visco-elastic properties. The HA which is at present commercially available is generally obtained from arian sources such as rooster combs but problems with this material include the likelihood of it being contaminated by viruses. Complex purification procedures are therefore needed and a suitable process is described in U.S. Pat. No. 4141973. However, the need for this extensive purification clearly adds to the production cost of the material.

Because of the problems associated with the isolation of HA from avian sources, attempts have been made to develop fermentation processes in which HA is produced. Although all species of Streptococcus produce HA, it is important to choose a species which is a good producer of HA and which is free of hyaluronidase activity.

U.S. Pat. No. 4517295 describes a fermentation process using *S. pyogenes* but the product has an average molecular weight of only 55,000. EP-A-0144019 describes an alternative fermentation process using *S. equi* which claims to produce a high molecular weight HA but the molecular weight is calculated by a non-standard method and cannot therefore easily be compared with molecular weights calculated by other methods. WO-A-8604355 and U.S. Pat. No. 4897349 both describe fermentation processes in which HA of high molecular weight is produced in good yield but in both of the processes, a pathogenic species of Streptococcus is used and so the HA product is likely to be unsuitable for use in medicine because of contamination by the bacterial toxins.

In addition, all of the prior art processes described are batch fermentation processes. There are various problems with batch fermentation processes and these include production of a contaminated product which is difficult to purify.

It would therefore be particularly advantageous to develop a fermentation process which is free from the usual disadvantages of batch fermentation and in which HA having a high molecular weight (for example several million) could be produced.

In a first aspect of the invention, therefore, there is provided a process for the production of HA by fermentation of Streptococcus, characterised in that the process comprises continuous fermentation of Streptococcus in a chemostat culture which is maintained at a pH of from 6.0 to 7.0, a dilution rate of 0.05 to 0.12 $h^{-1}$ and a dissolved oxygen tension of less than 1% saturation.

Continuous fermentation processes are known and the theory has been described by Herbert et al (1956) *J. Gen. Micro.*, 14, 602–622. The number of commercial continuous fermentation processes are limited because of the perceived difficulty of continuous fermentation processes over traditionally based batch processes. Also, continuous fermentation processes have traditionally been considered to be suited only for large production output, low product value facilities whereas batch culture has always been used for low production output high product value facilities such as those used to make HA.

The process of the invention overcomes various problems associated with traditional batch culture technique. In batch culture, as the Streptococcus approaches stationary phase, various degradation enzymes start to break down the cells releasing cell contents into the fermenter broth and this leads to purification difficulties. This does not occur if a continuous fermentation process is used since the fermentation medium is maintained in a steady state so that the expression of such enzymes is reduced. A further advantage of the steady state obtained with continuous fermentation is that the cell wall turnover is reduced which is advantageous because it has proved extremely difficult to separate HA from cell wall components which have been released into the fermentation medium. Finally, the use of continuous culture avoids the expression of various toxins which are expressed during the stationary phase of batch cultures. The use of a continuous fermentation process therefore allows for the production of a much purer product.

The HA produced by the process of the invention has an average molecular weight of from 1 to 3 million and under preferred conditions, the molecular weight is from 1.6 to 2.5 million. High molecular weight HA in solution has visco-elastic properties which make it extremely useful in a variety of clinical fields including wound treatment, ophthalmic surgery and orthopaedic surgery. HA is also potentially useful in a variety of non-medical fields.

If the HA produced by the process of the invention is to be useful in medicine, it is of course important that any contaminants should not be toxic. The species of Streptococcus used in the fermentation process should therefore preferably be one which is not a human pathogen in order to minimise the risk that any bacterial contaminants remaining in the product will then be toxic. In addition, the safety of the manufacturing facility is increased if a non pathogenic Streptococcus is used and an accidental leak from a fermenter will not cause serious health risks. A particularly suitable species for use in this fermentation process is *S. equi* although other species could of course be used.

Suitable strains of *S. equi* for use in the process will easily be selected by those skilled in the art using long term selection in the chemostat culture and choosing a stable, high yielding phenotypic variant suitable for long term culture by isolating from the culture, individual cells to use as seed for further fermentations. A sample of the culture may be streaked on to solid medium and colonies originating from individual (or a small number of) cells allowed to grow. We have found that the starting strain of *S. equi* may be improved by selecting fast growing colonies with large mucoid capsules having a stringy appearance when pulled with a loop. These colonies may be used to seed the fermenter for the next run. Preferably, they are first subcultured onto further plates and the same selection criteria applied to select seed-colonies.

A particularly suitable strain has been deposited by us under the Budapest Treaty at the National Collection of Industrial and Marine Bacteria (NCIMB) 23 Macher Drive, Aberdeen, Scotland AB2 1RY on 24 Oct. 1990 under the accession No NCIMB 40327.

The fermentation process of the invention takes place in a nutrient medium containing the following components:

an assimilable source of carbon;

a source of nitrogen;

sources of phosphorus, sodium, potassium, magnesium, iron, zinc and manganese;

sources of growth factors; and a source of sulphur.

Carbon may be supplied in the form of a sugar, particularly glucose, although sucrose can also be used. The source of nitrogen may be a non-toxic nitrogen containing salt, particularly a water soluble salt, for example, an ammonium salt such as ammonium chloride. The metals and phosphorus may also be supplied in the form of water soluble salts. The necessary growth factors are all contained in a source such as yeast extract which may also be the source of the sulphur which is required.

The nutrient medium may additionally contain sources of one or more of calcium, molybdenum, cobalt copper or boron.

The growth rate of the bacteria in the continuous fermentation process may be controlled by limiting the availability of one essential component of the nutrient medium, thus limiting biomass production but not energy conversion or polysaccharide formation. The supply of any of the essential components listed above may be limited but it is preferred to limit the supply of the sulphur.

The pH of the nutrient medium must, as mentioned above, be maintained within the range of 6.0 to 7.0. A preferred range is 6.0 to 6.4 and most favourable conditions are achieved when the pH is 6.2.

The pH of the medium may be maintained within the desired range by the addition of an alkali such as sodium hydroxide during the fermentation process. Any foaming which results may be controlled by the addition of a suitable non-toxic foaming agent, for example an agent based on polypropyleneglycol.

As discussed above, the nutrient medium is supplied to the fermentation zone at a dilution rate (flow rate per unit volume of the fermenter) of from 0.05 to 0.12 $h^{-1}$. The most favourable conditions occur when the dilution rate is about 0.07 $h^{-1}$. Effluent is withdrawn from the fermenter at a rate equal to the rate of supply of nutrient medium to the fermenter so as to maintain a constant volume of medium within the fermentation vessel. A constant physicochemical environment is maintained using automatic controllers which maintain constant optimum conditions for the selected strain of *S. equi* during long term continuous culture. The product is harvested from the effluent.

The culture of Streptococcus is carried out under microaerophilic conditions. Air or other oxygen containing gas may be pumped into the culture medium at a rate sufficient to maintain a dissolved oxygen tension in the fermentation medium of less than 1% saturation and preferably in the range of 0.1 to 0.5% saturation. The gas supplied to the fermentation medium must be sterile and, in the case where air is used, a suitable flow rate may be from 0.1 to 0.5 v.v.m. (volumes per fermenter volume per minute).

It is desirable that the fermentation is carried out with continuous agitation since the fermentation medium is viscous and thorough mixing of the medium is essential to eliminate "dead zones" in which growth of undesired non-HA producing strains of *S. equi* can occur.

The temperature of the fermentation medium should be maintained in the range of 30° to 40° C. but a preferable range is from 35° to 40° C. and the most suitable temperature is 37° C.

Under the preferred operating conditions, the process of the invention has yielded as much as 2.5 g of HA for every liter of fermentation medium and it is possible that even higher yields may be obtained. Stable culture conditions can be maintained for over 500 hours. The process therefore represents a considerable improvement over prior art batch fermentation processes.

After the fermentation process, the biomass is killed and the HA extracted with an aqueous medium containing an anionic surfactant. These two steps may take place either simultaneously or sequentially. A variety of means may be used to kill the biomass, including heat or a killing agent such as an antibacterial substance. A particularly suitable agent for killing the biomass is formaldehyde which may be used as the aqueous solution commonly known as formalin. A suitable concentration of the solution is from 0.5 to 1.5% (v/v). The surfactant may be added at a concentration of from 0.01 to 0.05% (w/v) and preferably at a concentration of 0.02% (w/v). A suitable surfactant for extracting the HA from the killed biomass is sodium dodecyl sulphate.

The biomass is kept in contact with the killing agent and the surfactant until substantially all the HA has been released from the cellular capsules and this may take from 10 to 24 hours, usually about 16 hours.

The residual biomass is then separated from the aqueous solution by filtration, for example using a plate and frame filter process and an appropriate filtration medium such as kieselguhr filter pads. It is necessary to clean or replace these filter pads during the fermentation process and a suitable time interval for this may be every 24 hours. An alternative filtration method which is particularly useful for large scale operation is to use a filter cartridge. Such cartridges have to be replaced at similar time intervals to the filter pads. After the filtration, a cell-free filtered solution of HA is obtained and this solution may be purified by diafiltration to remove low molecular weight impurities. These impurities are those derived from the production organism's metabolism, the residual components of the nutrient medium, residual killing agent and residual anionic surfactants. It is necessary in this step to use an ultra filtration membrane with an appropriate molecular weight cut off which is usually from 10,000 to 25,000 Daltons, and preferably 20,000 Daltons nominal molecular weight. Suitable membranes are based on polysulphones and are available commercially. The filtered solution containing the dissolved HA is diafiltered against from 8 to 20 volumes, preferably about 10 volumes of purified water and the filtrate is continuously discarded. Water of suitable purity has a conductivity of less than 10 $\mu Scm^{-1}$.

After the diafiltration, the molarity of purified solution of HA is adjusted to within the range of 0.18 to 0.24M, preferably 0.20M with respect to sodium chloride. The pH is also adjusted if necessary to a value of from 6.3 to 7.8, preferably from 7.0 to 7.5. The most favourable results are achieved when the pH is 7.2. The pH may be adjusted by the addition of a base such as sodium hydroxide or an appropriate buffer, particularly a phosphate buffer.

If a product of medical grade is required, the process may include an optional step of precipitating nucleic acids from the solution. This is achieved by the addition of a cationic surfactant for example a quaternary ammonium compound such as cetyl pyridinium chloride. The cationic surfactant may be added as a dilute aqueous solution; for example a 1% (w/v) solution of cetyl pyridinum chloride may be added in a volume ratio of 1:60 to the solution. The precipitated nucleic acid may then be removed by filtration through an appropriate filter medium ranging in pore size of from 3.2

μm to 0.2 μm but preferably from 1.2 μm to 0.2 μm. If this step is used, subsequent processing must be carried out under sterile conditions using pyrogen-free equipment.

After this optional stage, or, if the optional stage is not used, after the adjustment of the molarity and pH of the solution, HA is precipitated by the addition of a non-solvent, for example a lower alcohol such as isopropyl alcohol. The precipitated HA is filtered off and the filtrate discarded.

Further purification of the HA product can be achieved by redissolving the HA in sodium chloride solution and then reprecipitating by addition of a non-solvent in the same way as described above. The sodium chloride solution must have a molarity in the range of 0.18 to 0.24M, the most favourable value being 0.20M. The pH of the solution must be from 6.3 to 7.8 but is preferably 7.0 to 7.5 and most preferably 7.2. The solution may be buffered, for example with a phosphate buffer.

In a second aspect of the invention there is provided hyaluronic acid produced by the process of the first aspect. This HA has an average molecular weight of at least 1 million and the range of molecular weights of the product is preferably from 1.6 to 2.5 million.

In a third aspect of the invention, there is provided *Streptococcus equi* of the strain NCIMB 40327.

The invention will now be further described with reference to the following examples.

EXAMPLE 1

A growth medium for *S. equi* is formulated as follows:

Glucose: 60.00 g

Yeast extract: 6.25 g (Oxoid L21)

Sodium dihydrogen phosphate ($2H_2O$): 2.02 g

Ammonium chloride: 2.14 g

Potassium chloride: 0.71 g

Citric acid: 0.42 g

Magnesium oxide: 0.40 g

Calcium carbonate: 0.10 g

Sodium molybdate ($2H_2O$): 2.42 mg

Ferrous chloride ($6H_2O$): 10.80 mg

Cobalt chloride ($6H_2O$): 0.95 mg

Copper chloride ($2H_2O$): 0.32 mg

Zinc oxide: 0.81 mg

Manganese chloride ($6H_2O$): 4.00 mg

Boric acid: 0.12 mg

Conc. Hydrochloric acid: 0.178 mL

This medium is made up to 1 L with purified water. It is then sterilized by filtration through an 0.22 μm absolute rated filter.

The fermentation medium is pumped continuously into the fermenter at a flow rate, in relation to the fermenter volume, of 0.07 $h^{-1}$. The medium is aerated with sterile air which has been filtered through an 0.2 μm absolute rated filter. The air flow rate is maintained at 0.2 v.v.m. and a dissolved oxygen tension is maintained in the fermenter broth at 0.2% saturation. *Streptococcus equi* is grown in this culture medium at 37° C. The pH is maintained at 6.2 by automatically controlled additions of sodium hydroxide. Foam generation is controlled by addition as necessary of a polypropylene glycol based antifoam.

Fermentation medium is continuously withdrawn from the fermenter at the same rate as the fresh medium is fed in. This effluent contains about 2.5 $gL^{-1}$ of hyaluronic acid. Sodium dodecyl sulphate and formalin solution are continuously fed into the effluent from the fermenter to achieve final concentrations of 0.025% (w/v) of sodium dodecyl sulphate and 1% (v/v) of formalin. Mixing of the effluent and the sodium dodecyl sulphate/formalin streams takes place in an in-line static mixer. The contact time is 16 hours and, after mixing, the stream passes through a vessel designed for this residence time.

After release of the hyaluronic acid into the aqueous medium, the residual biomass is removed continuously by depth filtration in a cartridge filter using filters of appropriate pore size. Duplicate filter units are used to allow periodic diversion of the product flow to a clean filter, thus allowing cleaning and replacement of used filters. The filter units are sized to allow up to 24 hours operation before flow diversion is required.

The solution from which the cells have been removed is then processed by diafiltration against purified water to remove residual materials from the culture medium, sodium dodecyl sulphate and formalin. This diafiltration is operated using a polysulphone based ultrafiltration membrane with a 20,000 Dalton nominal molecular weight cut off. The solution is diafiltered against ten volumes of water having a conductivity of less than 10 μS $cm^{-1}$, and the filtrate is continuously discarded. After diafiltration, sodium chloride (final concentration 0.2M) is added to the solution obtained and the pH adjusted to 7.2 by addition of phosphate buffer ($Na_2HPO_4$, 0.22$gL^{-1}$; $NaH_2PO_4.2H_2O$, 0.045$gL^{-1}$). A 1% (w/v) solution of cetyl pyridinium chloride is then added in a ratio of about 1:60 by volume. The nucleic acids thus precipitated are removed by pumping the solution through 1.2μm and 0.2μm (absolute rated) depth filters arranged in series. The filtered solution of hyaluronic acid thus obtained is then continuously mixed in line with a metered flow of isopropyl alcohol at a flow ratio of 1:2. The mixing is performed in a static mixer and the precipitated hyaluronic acid is separated from the aqueous solution in a basket filter. The filtrate is discarded. The recovered hyaluronic acid is redissolved in 0.2M sodium chloride solution buffered at pH 7.2 with phosphate ($Na_2HPO_4$, 0.022$gL^{-1}$; $NaH_2PO_4.2H_2O$, 0.045$gL^{-1}$) to give an HA concentration of 0.2% w/v). The hyaluronic acid is again precipitated from this solution by addition of isopropyl alcohol in the same way as previously.

The precipitated hyaluronic acid is washed with isopropyl alcohol and the washings are discarded. Final traces of isopropyl alcohol are removed by drying in air under sterile conditions. All the purification procedures are carried out at ambient temperature.

A medical grade solution may be made by dissolving hyaluronic acid produced in the manner described in 0.15M sterile saline solution buffered with the phosphate buffer mentioned above, pH 7.3 to give a 1% (w/v) solution of hyaluronic acid. The sodium hyaluronate solution so prepared has an average molecular weight of 1.6 to 2.5×$10^6$ Da as determined by low angle laser light scattering techniques and viscometry. The solution has a protein content of less than 0.2% (w/w) and a nucleotide level of less than 0.15% (w/w). The 1% (w/v) solution shows a U.V. absorption of 0.14 AU at 260 nm and 0.1 AU at 280 nm. The viscosity of the solution is 159 Pa.s at zero shear falling to less than 1 Pa.s at 1000 $s^{-1}$.

The following example demonstrates a method of selecting suitable strains of *S. equi* for use in the fermentation process.

EXAMPLE 2

A solid medium for growth of *S. equi* is formulated as follows:

Glucose: 20 g
Yeast extract: 5 g (Oxoid L21)
Agar: 15 g (Oxoid L 13 Agar No. 3)
Di-potassium hydrogen orthophosphate anhydrous: 1.706 g
Potassium dihydrogen orthophosphate: 1.388 g
Sodium dihydrogen orthophosphate: 2.92 g
Ammonium chloride: 5.01 g
Potassium chloride: 372 mg
Citric acid: 420 mg
Magnesium oxide: 50.4 mg
Calcium carbonate: 10 mg
Sodium molybdate: 2.4 mg
Ferrous chloride ($6H_2O$): 270 mg
Cobalt chloride ($6H_2O$): 2.37 mg
Copper chloride ($2H_2O$): 0.85 mg
Zinc oxide: 2.05 mg
Manganese chloride ($4H_2O$): 10 mg
Boric acid: 0.3 mg
Conc. Hydrochloric acid: 0.24 mL The glucose is dissolved in 50 mL of water, the yeast extract in 100 mL and the agar/salts dissolved in 820 mL of water, sterilized separately by autoclaving at 121° C. for 15 minutes and then mixed together prior to pouring the plates.

Samples of *S. equi* from a fermentation experiment performed as described in Example 1 were obtained for strain improvement. Strain improvement was carried out by selecting large fast growing domed colonies with large mucoid capsules having a stringy appearance when pulled with a loop. These colonies were subcultured onto further plates where the same selection criteria were applied.

It can therefore be seen that the process of the invention provides an economically viable fermentation process for obtaining pure HA of high molecular weight and therefore represents a significant improvement over prior art processes.

We claim:

1. A process for the production of hyaluronic acid by fermentation of Streptococcus in a nutrient medium containing:

an assimilable source of carbon;

a source of nitrogen;

sources of phosphorus, sodium, potassium, magnesium, iron, zinc and manganese;

sources of growth factors; and a source of sulphur, characterised in that the process comprises continuous fermentation of Streptococcus in a chemostat culture which is maintained at a pH of from 6.0 to 7.0, a dilution rate of 0.05 to 0.12 $h^{-1}$ and a dissolved oxygen tension of less than 1% saturation.

2. A process for the production of hyaluronic acid comprising:

(a) culturing Streptococcus by fermentation in a nutrient medium containing:

an assimilable source of carbon;

a source of nitrogen;

sources of phosphorus, sodium, potassium, magnesium, iron, zinc and manganese;

sources of growth factors; and a source of sulphur, characterized in that the process comprises continuous fermentation of Streptococcus in a chemostat culture which is maintained at a pH of from 6.0 to 7.0, a dilution rate of 0.05 to 0.12 $h^{-1}$, and a dissolved oxygen tension of less than 1% saturation to produce a biomass containing hyaluronic acid, and (b) recovering said hyaluronic acid from said biomass.

3. The process of claim 2, wherein said species of Streptococcus is not pathogenic to humans.

4. The process of claim 2, wherein said source of carbon in the nutrient medium is a sugar.

5. The process of claim 2, wherein said source of nitrogen in the nutrient medium is an ammonium salt.

6. The process of claim 2, wherein said sources of phosphorus, sodium, potassium, magnesium, iron, zinc and manganese in the nutrient medium are water soluble salts of those elements.

7. The process of claim 2, wherein said source of growth factors and sulphur in the nutrient medium is yeast extract.

8. The process of claim 2, wherein said nutrient medium further comprises sources of one or more members selected from the group consisting of calcium, molybdenum, cobalt, copper and boron.

9. The process of claim 2, wherein said sulphur is a limiting component.

10. The process of claim 2, wherein said nutrient medium contains limited amounts of one or more members selected from the group consisting of carbon, nitrogen, phosphorous, sodium, potassium, magnesium, iron, zinc, manganese, growth factors and sulphur.

11. The process of claim 2, wherein said pH of said nutrient medium is 6.2.

12. The process of claim 2, wherein said dilution rate is 0.07 $h^{-1}$.

13. The process of claim 2, wherein said dissolved oxygen tension in said chemostat culture is in the range of 0.1 to 0.5% saturation.

14. The process of claim 2, wherein said continuous fermentation is carried out with continuous agitation.

15. The process of claim 2, wherein the temperature is maintained in the range of 35° to 40° C.

16. The process of claim 2, wherein step (b) further comprises killing the biomass and extracting hyaluronic acid from said killed biomass.

17. The process of claim 16, wherein said biomass is killed using an aqueous solution of formaldehyde.

18. The process of claim 16, wherein said hyaluronic acid is extracted from said killed biomass using an anionic surfactant.

19. The process of claim 18, wherein said anionic surfactant is sodium dodecyl sulphate.

20. The process of claim 16, further comprising the step of filtering said extracted hyaluronic acid to remove said killed biomass.

21. The process of claim 20, further comprising the step of purifying said filtered solution of extracted hyaluronic acid by diafiltration to remove low molecular weight impurities.

22. The process of claim 21, further comprising the steps of:

(i) adjusting the molarity of said purified solution of hyaluronic acid with respect to sodium chloride of said purified solution to within the range of 0.18 to 0.24M;

(ii) adjusting the pH of said solution of purified hyaluronic acid to from 6.3 to 7.8; and (iii) precipitating said purified hyaluronic acid by the addition of a non-solvent.

23. The process of claim 22, comprising the further step (iv) of precipitating nucleic acids from said solution of purified hyaluronic acid by the addition of a cationic surfactant.

24. The process of claim 23, wherein said cationic surfactant is a quarternary ammonium compound.

25. The process of claim 24, wherein said quaternary ammonium compound is cetyl pyridinum chloride.

26. The process of claim 22, wherein said non-solvent is a member selected from the group comprising methanol, ethanol and isopropyl alcohol.

27. An isolated culture of the microorganism *Streptococcus equi* having all of the identifying characteristics of NCIMB 40327.

* * * * *